US010175226B2

(12) United States Patent
Gordon et al.

(10) Patent No.: US 10,175,226 B2
(45) Date of Patent: Jan. 8, 2019

(54) DETECTION AND QUANTIFICATION OF ACETYLAMANTADINE IN URINE SAMPLES

(71) Applicant: BioMark Technologies, Inc., Richmond (CA)

(72) Inventors: Reuven Gordon, Victoria (CA); Brian Cheng, Chesterfield, MO (US); Rashid Bux, Vancouver (CA); Bram Ramjiawan, Winnipeg (CA); Aftab Ahmed, Waterloo (CA); Fraser Alan Hof, Victoria (CA)

(73) Assignee: BioMark Technologies, Inc., Richmond, British Columbia (CA)

(*) Notice: Subject to any disclaimer, the term of this patent is extended or adjusted under 35 U.S.C. 154(b) by 0 days.

(21) Appl. No.: 15/645,994

(22) Filed: Jul. 10, 2017

(65) Prior Publication Data

US 2017/0328881 A1   Nov. 16, 2017

Related U.S. Application Data

(63) Continuation of application No. 14/776,702, filed as application No. PCT/CA2014/050273 on Mar. 14, 2014.

(Continued)

(51) Int. Cl.
*G01N 33/493* (2006.01)
*G01N 21/65* (2006.01)
(Continued)

(52) U.S. Cl.
CPC ......... *G01N 33/493* (2013.01); *G01N 1/4055* (2013.01); *G01N 21/65* (2013.01); *G01N 21/658* (2013.01); *G01N 33/574* (2013.01); *A61B 5/0075* (2013.01); *C12Q 1/48* (2013.01); *G01N 15/0205* (2013.01); *G01N 15/1434* (2013.01);
(Continued)

(58) Field of Classification Search
CPC .. G01N 1/4055; G01N 21/658; G01N 33/493; G01N 21/65; G01N 33/574; G01N 33/57484; G01N 15/0205; G01N 15/1434; G01N 27/44721; G01N 27/74; A61B 5/0075; C12Q 1/48
See application file for complete search history.

(56) References Cited

U.S. PATENT DOCUMENTS 6,811,967 B2   11/2004   Sitar et al.
2002/0132280 A1*   9/2002   Sitar ..................... C12Q 1/48
435/15

(Continued)

FOREIGN PATENT DOCUMENTS

WO   WO-2012151702 A1 *   11/2012   ............. C07K 16/44

OTHER PUBLICATIONS

WIPO, Canadian International Search Authority, International Search Report and Written Opinion dated Jul. 15, 2014 in International Patent Application No. PCT/CA2014/050273, 8 pages.

(Continued)

*Primary Examiner* — Jennifer Wecker
(74) *Attorney, Agent, or Firm* — Inskeep IP Group, Inc.

(57) ABSTRACT

A method for quantifying acetylamantadine in a urine sample comprises eluting acetylamantadine from the urine sample using solid phase extraction and quantifying the acetylamantadine eluted from the urine sample using Raman spectroscopy.

6 Claims, 2 Drawing Sheets

Related U.S. Application Data

(60) Provisional application No. 61/785,159, filed on Mar. 14, 2013.

(51) Int. Cl.
  *G01N 1/40* (2006.01)
  *G01N 33/574* (2006.01)
  *A61B 5/00* (2006.01)
  *G01N 27/74* (2006.01)
  *C12Q 1/48* (2006.01)
  *G01N 15/02* (2006.01)
  *G01N 15/14* (2006.01)
  *G01N 27/447* (2006.01)

(52) U.S. Cl.
  CPC ....... *G01N 27/44721* (2013.01); *G01N 27/74* (2013.01); *G01N 33/57484* (2013.01)

(56) References Cited

U.S. PATENT DOCUMENTS

| | | | | |
|---|---|---|---|---|
| 2006/0250613 | A1* | 11/2006 | Demuth | G01J 3/32 356/301 |
| 2008/0002198 | A1* | 1/2008 | Sun | G01J 3/36 356/301 |
| 2010/0085564 | A1* | 4/2010 | Guo | G01J 3/02 356/301 |
| 2010/0268473 | A1* | 10/2010 | Tripp | C12Q 1/6883 702/19 |
| 2012/0184451 | A1* | 7/2012 | Singamaneni | B82Y 5/00 506/9 |

OTHER PUBLICATIONS

Sitar, D.S. et al., "Amantadine acetylation as a biomarker for malignancy," *American Sociate for Clinical Pharmacology and Therapeutics*, Feb. 2006, PI-12, 1 page.

Moreira, L.M. et al., "Raman spectroscopy: A powerful technique for biochemical analysis and diagnosis," *Spectroscopy*, vol. 22, Issue 1, Jan. 1, 2008, pp. 1-19 (19 pages).

Bras, A.P.M. et al., "Spermidine/Spermine $N^1$-Acetyltransferase Catalyzes Amantadine Acetylation," *Drug Metabolism and Disposition*, vol. 29, No. 5, May 1, 2001, pp. 676-680 (5 pages).

Zhai, Fuli et al., "Rapid Determination of Ractopamine in Swine Urine Using Surface-Enhanced Raman Spectroscopy," *J. Agric. Food Chem.*, 2011, 59(18), Aug. 16, 2011, pp. 10023-10027, 5 pages.

\* cited by examiner

Open air evaporation          Slow evaporation

DETECTION AND QUANTIFICATION OF ACETYLAMANTADINE IN URINE SAMPLES

RELATED APPLICATIONS

This application is a continuation of and claims priority to U.S. patent application Ser. No. 14/776,702 filed Sep. 14, 2015 entitled Detection And Quantification Of Acetylamantadine In Urine Samples, which is the U.S. National Phase of and claims priority to International Patent Application No. PCT/CA2014/050273, International Filing Date Mar. 14, 2014, entitled Detection And Quantification Of Acetylamantadine In Urine Samples, and claims benefit of and priority to U.S. Provisional Application Ser. No. 61/785,159 filed Mar. 14, 2013 entitled Detection And Quantification Of Acetylamantadine In Urine Samples, all of which are hereby incorporated herein by reference in their entireties.

BACKGROUND OF THE INVENTION

Field of the Invention

The present invention relates to the detection and quantification of biomarkers and, in particular, to the detection and quantification of acetylamantadine in urine samples.

Description of the Related Art

Liquid chromatography mass spectrometry has been successfully employed to detect and quantify extremely low concentrations of acetylamantadine in biological samples such as urine. This may facilitate the diagnosis of cancer at an early stage as the quantification of acetylated forms of spermidine/spermine $N^1$-acetyltransferase (SSAT) including amantadine may be used to detect various pathological conditions including cancer as disclosed in U.S. Pat. No. 6,811,967 which issued to Sitar et al. on Nov. 4, 2004, and the full disclosure of which is incorporated herein by reference. However, the detection and quantification of acetylamantadine using liquid chromatography mass spectrometry is relatively time consuming and costly. There is accordingly a need for an efficient and cost effective method for detecting and quantifying acetylamantadine to allow for rapid economical testing.

SUMMARY OF THE INVENTION

It is an object of the present invention to provide an improved method for detecting and quantifying acetylamantadine in urine samples.

There is accordingly provided a method for quantifying acetylamantadine in a urine sample. The method comprises eluting acetylamantadine from the urine sample using solid phase extraction and quantifying the acetylamantadine eluted from the urine sample using Raman spectroscopy.

The solid phase extraction may include eluting acetylamantadine with methanol. The quantification of the acetylamantadine eluted from the urine sample using Raman spectroscopy may include the use of substrate based, surface-enhanced Raman spectroscopy.

The method disclosed herein may be used to screen a patient for a pathological condition based on the quantification of acetylamantadine in the urine sample. The method disclosed herein may also be used to screen a patient for cancer based on the quantification of acetylamantadine in the urine sample.

The method disclosed herein may be used to detect and quantify acetylamantadine at a low cost.

BRIEF DESCRIPTIONS OF DRAWINGS

The invention will be more readily understood from the following description of the embodiments thereof given, by way of example only, with reference to the accompanying drawings, in which.

DESCRIPTIONS OF THE PREFERRED EMBODIMENTS

Figure 1:
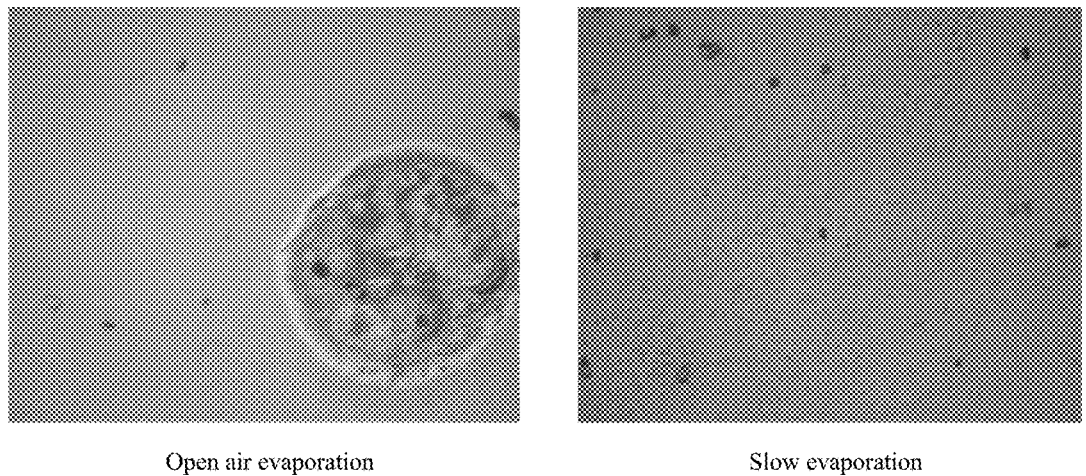
FIG. 1 shows the results of open air evaporation and slow evaporation of acetylamantadine in a methanol drop coated on a Surface Enhanced Raman Scattering (SERS) substrate for improvised coating and thus reliable quantification.

Disclosed herein is the use of Raman spectroscopy to identify and quantify acetylamantadine, a product of spermidine/spermine $N^1$-acetyltransferase (SSAT) metabolism, in urine samples. Urine is a concentrated solution of many salts, polar metabolites and multiple non-polar steroids. Expected concentration of acetylamantadine is about 1000 times smaller than that of amantadine in urine samples. The distinction between amantadine and acetylamantadine can be based on the vibrational band of a carbonyl group at an approximately 1600 $cm^{-1}$ wavenumber. There are a few other differences between the spectra of amantadine and acetylamantadine, but this Raman band may be of particular interest as it is present only in the spectrum of acetylamantadine.

A urine sample was prepared and different constituents of the urine sample were separated using solid phase extraction (SPE). The urine sample is accordingly pre-treated using solid phase extraction to remove impurities prior to using Raman spectroscopy to identify and quantify acetylamantadine present in the urine sample.

Urine Sample

Artificial urine comprising the following components of urine NaCl 8.00 g/L, KCl 1.64 g/L, $K_2SO_4$ 2.63 g/L, urea 13.40 g/L, and creatinine 1.50 g/L was used to prepare a urine sample having corticosterone 16.7 mM, amantadine 3.3 mM, and acetylamantadine 3.3 uM.

Solid Phase Extraction (SPE):

The urine sample was treated using solid phase extraction to remove salts and polar impurities, increase the acetylamantadine to amantadine ratio, and minimize contamination from non-polar steroids. The following protocol achieved all three aims using Strata X, Polymeric Reversed Phase from Phenomenex Inc of 411 Madrid Avenue, Torrance, Calif., 90501-1430.

(1) Prime: 2 mL MeOH, 2 mL deionized $H_2O$, 2 mL 50 mM pH 7.0 phosphate buffer.

(2) Load: Combine 2 mL of urine sample with 2 mL of 50 mM pH 7.0 phosphate buffer and load onto SPE cartridge.

(3) Wash 1: 2 mL deionized $H_2O$, 2×1.5 mL 50 mM pH 7.0 phosphate buffer (salts and polar metabolites elute with this fraction).

(4) Wash 2: 2×2 mL 40% methanol in H$_2$O (amantadine elutes with this fraction while acetylamantadine and the less polar steroid corticosterone is retained).
(5) Wash 3: 2 mL 100% methanol (acetylamantadine elutes with this fraction while corticosterone is retained).
(6) Dry column by flushing air through it for a few minutes.
(7) Eluent: 2 mL ethyl acetate (corticosterone elutes).

Coating of Acetylamantadine Over Surface Enhanced Raman Scattering (SERS) Substrate:

Acetylamantadine in methanol, obtained from Wash 3 of SPE protocol above, is drop coated on the SERS substrate for Raman measurements. In this example, the SERS substrate was a Klarite® SERS substrate from Renishaw Inc. of 5277 Trillium Boulevard, Hoffman Estates, Illinois, 60192. Uniform coating of acetylamantadine over the SERS substrate assists in reliable quantification. It was observed that slow evaporation of methanol results in improved coating of acetylamantadine over the substrate. FIG. 1 shows the results of open air evaporation and slow evaporation where the air flow is restricted. It can be seen that slow evaporation results in uniform coating.

Raman Measurements

Figure 2:
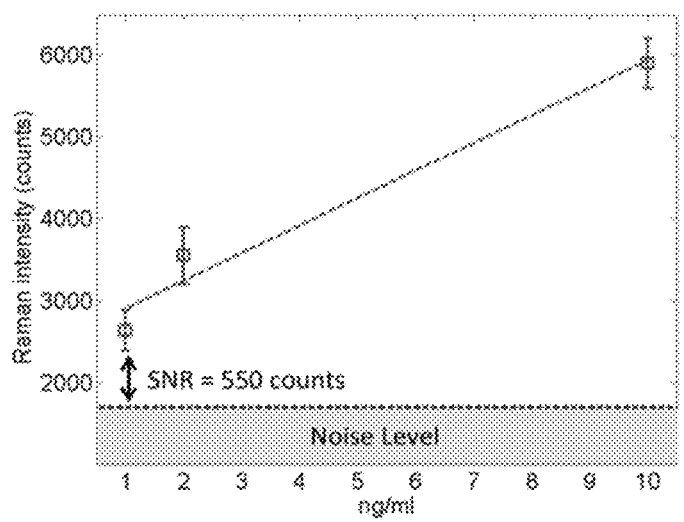
FIG. 2 shows quantification of acetylamantadine using a SERS substrate, such as Klarite®, to achieve a sensitivity of 1 ng/m L.

In this example, 30 uL of acetylamantadine in methanol was drop coated on the SERS substrate and allowed to dry slowly. A Raman map of 170 mesh points was collected with 1 second of integration at each mesh point. Out of the 170 spectra, only those were retained which showed Raman peaks, the rest were neglected. FIG. 2 shows the quantification based on the 1600 cm$^{-1}$ band. The required resolution and limit of detection of 1 ng/mL is achieved with adequate signal to noise ratio. It will however be understood by a person skilled in the art that it is desirable to use a number of different peaks to create a calibration curve because different peaks will result in result in calibration curves having slightly different slopes.

Raman Data and Analysis Used to Create a Calibration Curve

Figure 3:
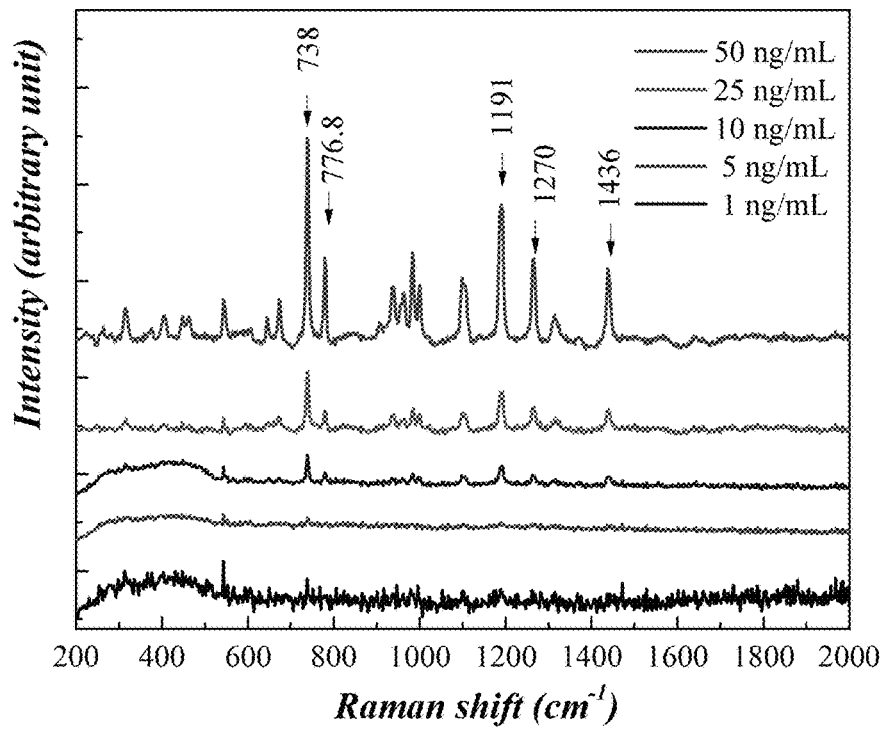
FIG. 3 shows Raman spectra for different concentrations of acetylamantadine in a methanol taken with the methanol evaporated and using a Klarite® substrate.

FIG. 3 shows Raman measurements for acetylamantadine in methanol in the following concentrations 1 ng/mL, 5 g/mL, 10 ng/mL, 25 ng/mL and 50 ng/mL which were prepared using standard chemistry techniques to dissolve acetylamantadine in methanol. Five peaks in the Raman spectra were chosen for each concentration, namely, 738 cm$^{-1}$, 776.8 cm$^{-1}$, 1198 cm$^{-1}$, 1210 cm$^{-1}$ and 1436 cm$^{-1}$.

Figure 4:
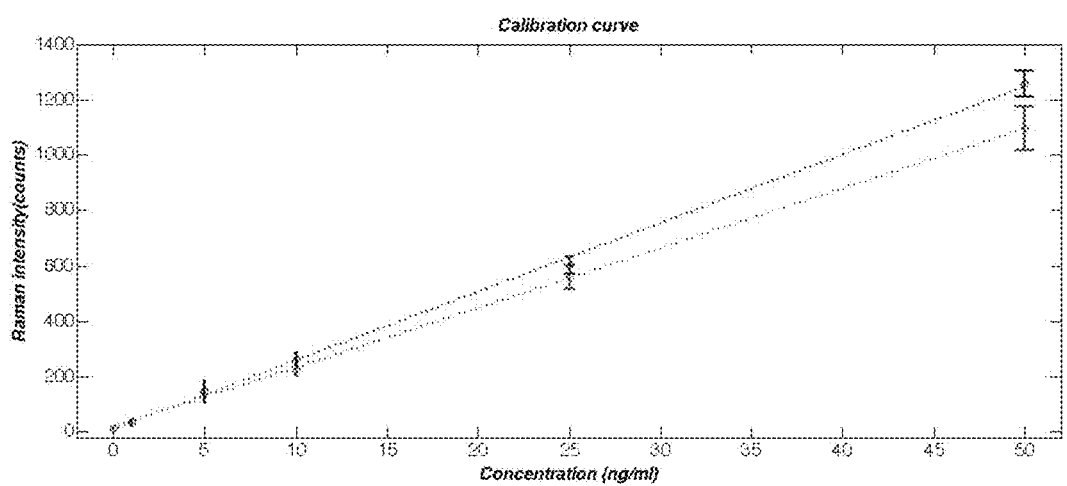
FIG. 4 shows a calibration curve based on the Raman spectra of FIG. 3 in which the bottom line is the original data and the top line is the revalidation.

Each peak was separated into a peak area and an adjacent area. Ten points were chosen in each peak area and adjacent area. The points were integrated and the number sum of peak area minus number sum of its adjacent area was used to get the intensity for each peak. It was then possible to get the Raman intensity for each concentration by integrating the five peaks as shown below.

$$\sum_{n=5} \left( \sum_{n\_peak=10} I_{peak} - \sum_{n\_adjacent=10} I_{adjacent} \right)$$

Where $I_{peak}$ is the intensities in peak area and $I_{adjacent}$ is the intensities in adjacent area. The sum of intensities for each concentration were then plotted to create the calibration curves shown in FIG. 4 which also shows the revalidation of the analysis. The calibration curve may be used to detect and quantify the acetylamantadine in a urine sample.

CONCLUSION

Results demonstrate that acetylamantadine can be extracted from urine samples using solid phase extraction. Raman spectroscopy can then be used to simultaneously detect and quantify the acetylamantadine with a sensitivity of 1 ng/mL in the urine sample to screen a patient for a pathological condition such as cancer.

It will be understood by a person skilled in the art that many of the details provided above are by way of example only, and are not intended to limit the scope of the invention which is to be determined with reference to the following claims.

What is claimed is:

1. A method for quantifying acetylamantadine in a urine sample, the method comprising:
    eluting acetylamantadine from the urine sample using solid phase extraction; and
    quantifying the acetylamantadine eluted from the urine sample using substrate based, surface enhanced Raman spectroscopy;
    wherein quantifying the acetylamantadine eluted from the urine sample using Raman spectroscopy includes quantifying the acetylamantadine with a sensitivity of 1 ng/mL.

2. The method as claimed in claim 1 wherein the solid phase extraction includes eluting acetylamantadine with methanol.

3. The method as claimed in claim 1 wherein quantifying the acetylamantadine eluted from the urine sample using Raman spectroscopy includes quantifying the acetylamantadine based on a 1600 cm$^{-1}$ band.

4. Use of the method as claimed in claim 1 to screen a patient for a pathological condition based on the quantification of acetylamantadine in the urine sample.

5. Use of the method as claimed in claim 1 to screen a patient for cancer based on the quantification of acetylamantadine in the urine sample.

6. An apparatus for screening a patient for a pathological condition comprising:
    a holding device for holding a urine sample;
    a solid phase extraction device that elutes acetylamantadine from said urine sample;
    a spectroscopy device that quantifies said eluted acetylamantadine using Raman spectroscopy with a sensitivity of 1 ng/mL.

* * * * *